US006207851B1

United States Patent
Luyken et al.

(10) Patent No.: US 6,207,851 B1
(45) Date of Patent: Mar. 27, 2001

(54) PROCESS FOR SIMULTANEOUSLY PREPARING 6-AMINOCAPRONITRILE AND HEXAMETHYLENE DIAMINE

(75) Inventors: Hermann Luyken, Ludwigshafen; Guido Voit, Schriesheim; Peter Bassler, Viernheim; Alwin Rehfinger, Mutterstadt; Rolf Fischer, Heidelberg, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/254,545
(22) PCT Filed: Aug. 21, 1997
(86) PCT No.: PCT/EP97/04544
    § 371 Date: Mar. 10, 1999
    § 102(e) Date: Mar. 10, 1999
(87) PCT Pub. No.: WO98/11060
    PCT Pub. Date: Mar. 19, 1998

(30) Foreign Application Priority Data

Sep. 10, 1996 (DE) .............................................. 196 36 766

(51) Int. Cl.$^7$ ................................................ C07C 255/00
(52) U.S. Cl. .......................................................... 558/459
(58) Field of Search ............................. 558/459; 564/463, 564/511

(56) References Cited

U.S. PATENT DOCUMENTS 3,696,153  10/1972  Kershaw et al. .

FOREIGN PATENT DOCUMENTS

| 2 131 448 | 12/1971 | (DE) . |
| 295 00222 | 7/1996 | (DE) . |
| 1094908 | 12/1967 | (GB) . |
| 1 354 565 | 5/1974 | (GB) . |
| 1 462 783 | 1/1977 | (GB) . |
| 2 212 155 | 7/1989 | (GB) . |
| 96/20931 | 7/1996 | (WO) . |

*Primary Examiner*—Joseph K. McKane
*Assistant Examiner*—Joseph Murray
(74) *Attorney, Agent, or Firm*—Keil & Weinkauf

(57) ABSTRACT

A process for coproduction of 6-aminocapronitrile and hexamethylenediamine starting from adiponitrile comprises (1) partially hydrogenating adiponitrile in the presence of a catalyst to obtain a mixture comprising 6-aminocapronitrile, hexamethylenediamine and adiponitrile, (2) removing 6-aminocapronitrile and hexamethylenediamine from the mixture, (3) adding to the portion comprising essentially adiponitrile from 0.01 to 10% by weight of an acid, based on adiponitrile, or an acidic ion exchanger and removing the adiponitrile from the mixture, and (4) recycling the adiponitrile into step (1).

12 Claims, 1 Drawing Sheet

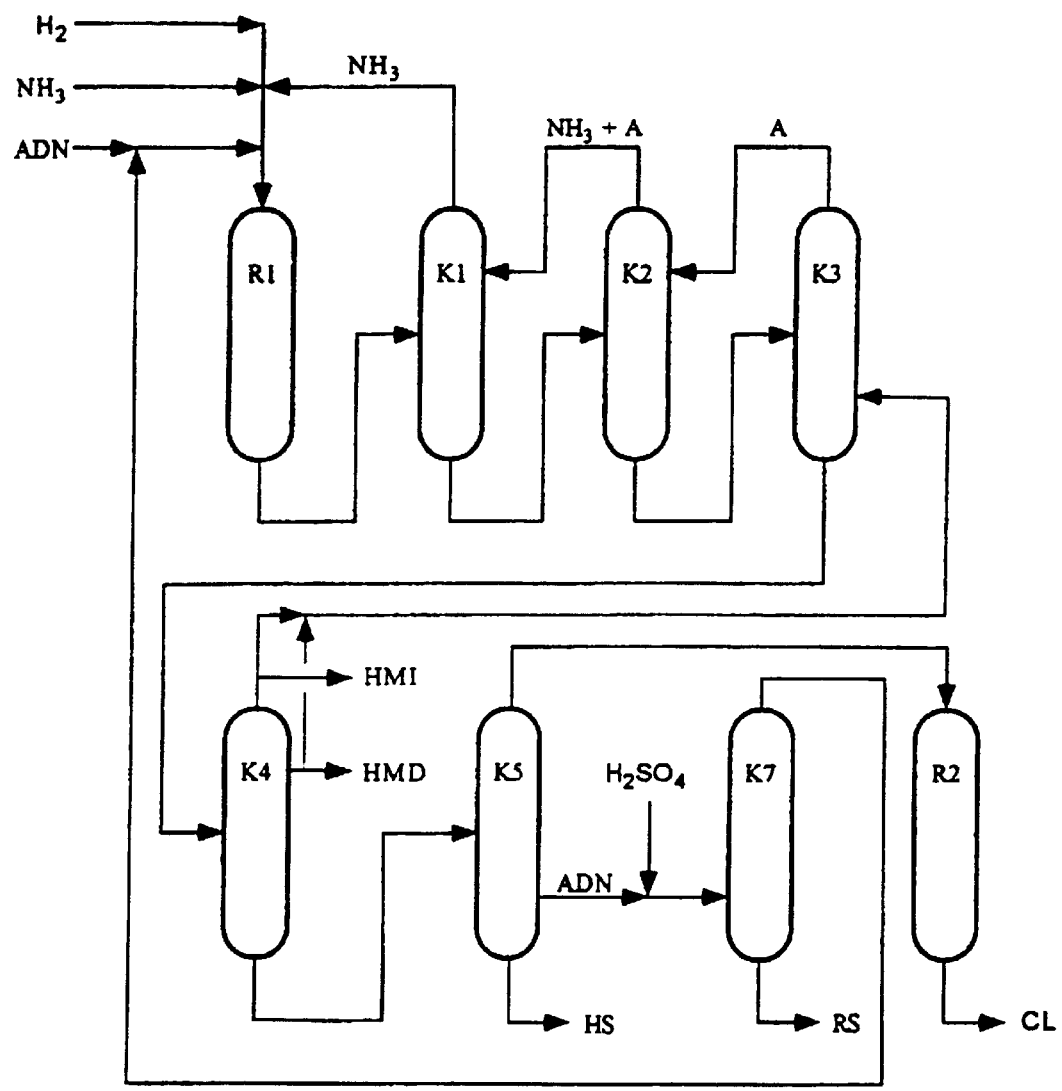

PROCESS FOR SIMULTANEOUSLY PREPARING 6-AMINOCAPRONITRILE AND HEXAMETHYLENE DIAMINE

This Application is a 371 of PCT/EP97/04544 filed Aug. 21, 1997.

DESCRIPTION

The present invention relates to a process for coproduction of 6-aminocapronitrile and hexamethylenediamine starting from adiponitrile by partial conversion and recovery of unconverted adiponitrile.

DE-A 19 500 222 and German Application 19 548 289.1 disclose a process for coproduction of 6-aminocapronitrile and hexamethylenediamine by hydrogenation of adiponitrile in the presence of a catalyst with partial conversion, the removal of hexamethylenediamine and 6-aminocapronitrile from the mixture and conversion of 6-aminocapronitrile into caprolactam and also recycling into the process of a portion consisting essentially of adiponitrile. The disadvantage of this process is that the recycled stream consisting essentially of adiponitrile comprises by-products of adiponitrile hydrogenation, especially amines such as 1-amino-2-cyanocyclopentene (ACCPE), 2-(5-cyanopentylamino) tetrahydroazepine (CPATRA) and bishexamethylenetriamine (BHMTA).

The by-products cannot be removed from adiponitrile by distillation in the processes described because of the formation of azeotropes or quasi-azeotropes, but build up in the process as a result of the recycling. ACCPE recycled into the hydrogenation forms 2-aminomethylcyclopentylamine (AMCPA), which contaminates the hexamethylenediamine product. It is known from U.S. Pat. No. 3,696,153 that AMCPA is very difficult to separate from hexamethylenediamine.

It is an object of the present invention to provide a process for coproduction of 6-aminocapronitrile and hexamethylenediamine from adiponitrile by partial conversion and recovery of unconverted adiponitrile without the disadvantages mentioned and whereby the unconverted adiponitrile is technically simple and economical to separate off and purify.

We have found that this object is achieved by a process for coproduction of 6-aminocapronitrile and hexamethylenediamine starting from adiponitrile, which comprises (1) partially hydrogenating adiponitrile in the presence of a catalyst to obtain a mixture comprising 6-aminocapronitrile, hexamethylenediamine and adiponitrile, (2) removing 6-aminocapronitrile and hexamethylenediamine from the mixture, (3) adding to the portion comprising essentially adiponitrile from 0.01 to 10% by weight of an acid, based on adiponitrile, or an acidic ion exchanger and removing the adiponitrile from the mixture, and (4) recycling the adiponitrile into step (1).

The partial hydrogenation of adiponitrile can be carried out by one of the known processes, for example by one of the abovementioned processes described in U.S. Pat. No. 4,601,859, U.S. Pat. No. 2,762,835, U.S. Pat. No. 2,208,598, DE-A 848 654, DE-A 954 416, DE-A 4 235 466 or WO 92/21650, by effecting the hydrogenation in general in the presence of nickel-, cobalt-, iron- or rhodium-containing catalysts. The catalysts may be used in the form of supported catalysts or unsupported catalysts. Examples of suitable catalyst carriers are alumina, silica, titanium dioxide, magnesium oxide, active carbons and spinels. Examples of suitable unsupported catalysts are Raney nickel and Raney cobalt.

The catalyst space velocity is usually chosen in the range from 0.05 to 10, preferably from 0.1 to 5, kg of adiponitrile per 1 of catalyst per hour.

Hydrogenation is carried out, as a rule, at from 20 to 200° C., preferably from 50 to 150° C., and at hydrogen partial pressures of from 0.1 to 40, preferably from 0.5 to 30, MPa.

The hydrogenation is preferably carried out in the presence of a solvent, in particular ammonia. The amount of ammonia is chosen in general in the range from 0.1 to 10, preferably from 0.5 to 3, kg of ammonia per kg of adiponitrile.

The molar ratio of 6-aminocapronitrile to hexamethylenediamine and hence the molar ratio of caprolactam to hexamethylenediamine can be controlled by the adiponitrile conversion chosen in each case. Adiponitrile conversions of from 10 to 90%, preferably from 30 to 80%, are preferably employed in order to obtain high 6-aminocapronitrile selectivities.

As a rule, the sum total of 6-aminocapronitrile and hexamethylenediamine is from 95 to 99%, depending on the catalyst and reaction conditions, hexamethyleneimine being the most important by-product in terms of quantity.

In a preferred embodiment, the reaction is carried out in the presence of ammonia and lithium hydroxide or a lithium compound which forms lithium hydroxide under the reaction conditions, at from 40 to 120° C., preferably from 50 to 100° C., particularly preferably from 60 to 90° C.; the pressure is chosen in general in the range from 2 to 12, preferably from 3 to 10, particularly preferably from 4 to 8, MPa. The residence times are essentially dependent on the desired yield, the selectivity and the desired conversion; usually, the residence time is chosen so that a maximum yield is achieved, for example in the range from 50 to 275, preferably from 70 to 200, minutes.

The pressure and temperature ranges are preferably chosen so that the reaction can be carried out in the liquid phase.

Ammonia is used in general in an amount such that the weight ratio of ammonia to dinitrile is from 9:1 to 0.1:1, preferably from 2.3:1 to 0.25:1, particularly preferably from 1.5:1 to 0.4:1.

The amount of lithium hydroxide is chosen as a rule in the range from 0.1 to 20, preferably from 1 to 10, % by weight, based on the amount of catalyst used.

Examples of lithium compounds which form lithium hydroxide under the reaction conditions are lithium metal and alkyllithium and aryllithium compounds such as n-butyllithium and phenyllithium. The amount of these compounds is chosen in general so that the abovementioned amount of lithium hydroxide is obtained.

Preferred catalysts are nickel-, ruthenium-, rhodium-, iron- and cobalt-containing compounds, preferably those of the Raney type, in particular Raney nickel and Raney cobalt. The catalysts may also be used in the form of supported catalysts, carriers which may be used being, for example, alumina, silica, zinc oxide, active carbon and titanium dioxide (cf. Appl. Het. Cat. (1987), 106–122; Catalysis 4 (1981), 1–30). Raney nickel (for example from BASF AG, Degussa and Grace) is particularly preferred.

The nickel, ruthenium, rhodium, iron and cobalt catalysts may be modified with metals of groups VIB (Cr, Mo, W) and VIII (Fe, Ru, Os, Co (only in the case of nickel), Rh, Ir, Pd, Pt) of the Periodic Table. Observations to date have shown that the use of, in particular, modified Raney nickel catalysts, for example modified with chromium and/or iron, leads to higher aminonitrile selectivities (for preparation, cf. DE-A 2 260 978 and Bull. Soc. Chem. 13 (1946), 208).

The amount of catalyst is chosen in general so that the amount of cobalt, ruthenium, rhodium, iron or nickel is from 1 to 50, preferably from 5 to 20, % by weight, based on the amount of dinitrile used.

The catalysts may be used as fixed-bed catalysts by the liquid phase or trickle-bed procedure or as suspended catalysts.

In a further preferred embodiment, adiponitrile is partially hydrogenated to 6-aminocapronitrile at elevated temperatures and high pressure in the presence of a solvent and of a catalyst which comprises (a) a compound based on a metal selected from the group consisting of nickel, cobalt, iron, ruthenium and rhodium, (b) from 0.01 to 25, preferably from 0.1 to 5, % by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and (c) from 0 to 5, preferably from 0.1 to 3, % by weight, based on (a), of a compound based on an alkali metal or an alkaline earth metal, with the proviso that, if a compound based on only ruthenium or rhodium or ruthenium and rhodium or nickel and rhodium is chosen as component (a), said promoter (b) can, if desired, be dispensed with, and with the further proviso that said component (a) shall not be based on iron when said component (b) is aluminum.

Preferred catalysts are those in which the component (a) comprises at least one compound based on a metal selected from the group consisting of nickel, cobalt and iron, in an amount of from 10 to 95% by weight and ruthenium and/or rhodium in an amount of from 0.1 to 5% by weight, based in each case on the sum of components (a) to (c), component (b) comprises at least one promoter based on a metal selected from the group consisting of silver, copper, manganese, rhenium, lead and phosphorus, in an amount of from 0.1 to 5% by weight, based on (a), and component (c) comprises at least one compound based on the alkali metals and alkaline earth metals, selected from the group consisting of lithium, sodium, potassium, cesium, magnesium and calcium, in an amount of from 0.1 to 5% by weight.

Particularly preferred catalysts are:

catalyst A, comprising 90% by weight of cobalt oxide (CoO), 5% by weight of manganese oxide ($Mn_2O_3$), 3% by weight of phosphorus pentoxide and 2% by weight of sodium oxide ($Na_2O$), catalyst B, comprising 20% by weight of cobalt oxide (CoO), 5% by weight of manganese oxide ($Mn_2O_3$), 0.3% by weight of silver oxide ($Ag_2O$), 70% by weight of silica ($SiO_2$), 3.5% by weight of alumina ($Al_2O_3$), 0.4% by weight of iron oxide ($Fe_2O_3$), 0.4% by weight of magnesium oxide (MgO) and 0.4% by weight of calcium oxide (CaO), and catalyst C, comprising 20% by weight of nickel oxide (NiO), 67.42% by weight of silica ($SiO_2$), 3.7% by weight of alumina ($Al_2O_3$), 0.8% by weight of iron oxide ($Fe_2O_3$), 0.76% by weight of magnesium oxide (MgO), 1.92% by weight of calcium oxide (CaO), 3.4% by weight of sodium oxide ($Na_2O$) and 2.0% by weight of potassium oxide ($K_2O$).

Such catalysts are described for example in DE-A 195 002 22 and German Application 195 482 89.1.

Particularly preferred catalysts are those comprising a) a compound based on iron such as iron oxide, b) from 0 to 5% by weight, based on (a), of a promoter based on an element or 2, 3, 4 or 5 elements selected from the group consisting of aluminum, silicon, zirconium, vanadium and titanium, and c) from 0 to 5% by weight, preferably from 0.1 to 3% by weight, especially from 0.1 to 0.5% by weight, based on (a), of a compound based on an alkali or alkaline earth metal, preferably selected from the group consisting of lithium, sodium, potassium, rubidium, cesium, magnesium and calcium.

The catalysts which may be preferably used may be unsupported catalysts or supported catalysts. Examples of suitable carrier materials are porous oxides, such as alumina, silica, aluminosilicates, lanthanum oxide, titanium dioxide, zirconium dioxide, magnesium oxide, zinc oxide and zeolites, and active carbon or mixtures thereof.

The preparation is carried out as a rule by a procedure in which precursors of the components (a) are precipitated together with precursors of the promoters (components (b)) and, if desired, with precursors of the trace components (c) in the presence or absence of carrier materials (depending on the catalyst type desired), if desired the resulting catalyst precursor is processed to give extrudates or pellets and is dried and then calcined. Supported catalysts are generally also obtainable by impregnating the carrier with a solution of the components (a), (b) and, if desired, (c), it being possible to add the individual components simultaneously or in succession, or by spraying the components (a), (b) and, if desired, (c) onto the carrier by a method known per se.

Suitable precursors of the components (a) are as a rule readily water-soluble salts of the abovementioned metals, such as nitrates, chlorides, acetates, formates and sulfates, preferably nitrates.

Suitable precursors of the components (b) are as a rule readily water-soluble salts or complex salts of the abovementioned metals, such as nitrates, chlorides, acetates, formates and sulfates and in particular hexachloroplatinate, preferably nitrates and hexachloroplatinate.

Suitable precursors of the components (c) are as a rule readily water-soluble salts of the abovementioned alkali metals and alkaline earth metals, such as hydroxides, carbonates, nitrates, chlorides, acetates, formates and sulfates, preferably hydroxides and carbonates.

The precipitation is generally effected from aqueous solutions, alternatively by adding precipitating reagents, by changing the pH or by changing the temperature.

The catalyst precursor thus obtained is usually dried, generally at from 80 to 150° C., preferably from 80 to 120° C.

The calcination is usually carried out at from 150 to 500° C., preferably from 200 to 450° C., in a gas stream comprising air or nitrogen.

After calcination, the catalyst material obtained is generally exposed to a reducing atmosphere (activation), for example by exposing it for from 2 to 24 hours to a hydrogen atmosphere or a gas mixture containing hydrogen and an inert gas, such as nitrogen, at from 80 to 250° C., preferably from 80 to 180° C., in the case of catalysts based on ruthenium or rhodium as component (a) or at from 200 to 500° C., preferably from 250 to 400° C., in the case of catalysts based on one of the metals selected from the group consisting of nickel, cobalt and iron as component (a). The catalyst loading here is preferably 200 l per l of catalyst.

Advantageously, the activation of the catalyst is carried out directly in the synthesis reactor, since this usually dispenses with an otherwise necessary intermediate step, ie. the passivation of the surface, usually at from 20 to 80° C., preferably from 25 to 35° C., by means of oxygen/nitrogen mixtures, such as air. The activation of passivated catalysts is then preferably carried out in the synthesis reactor at from 180 to 500° C., preferably from 200 to 350° C., in a hydrogen-containing atmosphere.

The catalysts may be used as fixed-bed catalysts by the liquid phase or trickle-bed procedure or as suspended catalysts.

If the reaction is carried out in a suspension, temperatures of from 40 to 150° C., preferably from 50 to 100° C., particularly preferably from 60 to 90° C., are usually chosen; the pressure is chosen in general in the range from 2 to 30, preferably from 3 to 30, particularly preferably from 4 to 9, MPa. The residence times are essentially dependent on the desired yield, the selectivity and the desired conversion; usually, the residence time is chosen so that a maximum yield is achieved, for example in the range from 50 to 275, preferably from 70 to 200, minutes.

In the suspension procedure, preferably used solvents are ammonia, amines, diamines and triamines of 1 to 6 carbon atoms, such as trimethylamine, triethylamine, tripropylamine and tributylamine, or alcohols, in particular methanol and ethanol, particularly preferably ammonia. A dinitrile concentration of from 10 to 90, preferably from 30 to 80, particularly preferably from 40 to 70, % by weight, based on the sum of dinitrile and solvent, is advantageously chosen.

The amount of catalyst is chosen in general in the range from 1 to 50, preferably from 5 to 20, % by weight, based on the amount of dinitrile used.

The suspension hydrogenation may be carried out batchwise or, preferably, continuously, as a rule in the liquid phase.

The partial hydrogenation can also be carried out batchwise or continuously in a fixed-bed reactor by the trickle-bed or liquid phase procedure, a temperature of from 20 to 150° C., preferably from 30 to 90° C., and a pressure of, as a rule, from 2 to 40, preferably from 3 to 20, MPa usually being chosen. The partial hydrogenation is preferably carried out in the presence of a solvent, preferably ammonia, an amine, a diamine or a triamine of 1 to 6 carbon atoms, such as trimethylamine, triethylamine, tripropylamine or tributylamine, or an alcohol, preferably methanol or ethanol, particularly preferably ammonia. In a preferred embodiment, an ammonia content of from 1 to 10, preferably from 2 to 6, g per g of adiponitrile is chosen. A catalyst space velocity of from 0.1 to 2.0, preferably from 0.3 to 1.0, kg of adiponitrile per 1 per h is preferably chosen. Here too, the conversion and hence the selectivity can be controlled by changing the residence time.

BRIEF DESCRIPTION OF THE DRAWINGS

FIG. 1 depicts a flow diagram of the apparatus used to carry out the method of the present invention.

The partial hydrogenation can be carried out in a conventional reactor suitable for this purpose (R1 in the drawing).

The hydrogenation affords a mixture comprising 6-aminocapronitrile, hexamethylenediamine and adiponitrile.

The removal from the mixture of 6-aminocapronitrile, hexamethylenediamine and a portion comprising essentially adiponitrile can be effected in a conventional manner, preferably by distillation, for example as described in DE-A 195 002 22 or German Application 19 548 289.1, simultaneously or in succession.

The distillation in the first column (K1 in the drawing) is carried out by a method in which the mixture comprising essentially 6-aminocapronitrile, hexamethylenediamine, ammonia, adiponitrile and hexamethyleneimine, preferably a mixture comprising essentially from 1 to 70, preferably from 5 to 40, % by weight of 6-aminocapronitrile, from 1 to 70, preferably from 5 to 40, % by weight of adiponitrile,
from 0.1 to 70, preferably from 1 to 40, % by weight of hexamethylenediamine,
from 0.01 to 10, preferably from 0.05 to 5, % by weight of hexamethyleneimine and
from 5 to 95, preferably from 20 to 85, % by weight of ammonia, is carried out as a rule in a conventional distillation column at a bottom temperature of from 60 to 250° C., preferably from 100 to 200° C., and a pressure of from 5 to 30, preferably from 12 to 25, bar in the presence of one or more compounds A which are inert under the distillation conditions and boil at from 60 to 220° C. at 18 bar, to give ammonia as the top product and a bottom product I, the ammonia not being completely separated off.

Suitable compounds A are substances which are inert under the distillation conditions and have a boiling point of from 60 to 250° C., preferably from 60 to 150° C., at 18 bar. Examples are alkanes, cycloalkanes, aromatics, naphthenes, alcohols, ethers, nitriles and amines having the abovementioned properties, in particular $C_5$–$C_8$-alkanes and $C_2$–$C_4$-alkanols, particularly preferably n-pentane, cyclohexane, triethylamine, ethanol, acetonitrile, n-hexane, di-n-propyl ether, isopropanol, n-butylamine and benzene, very particularly preferably ethanol.

Compound A is usually added in an amount of from 0.1 to 50, preferably from 1 to 10, % by weight, based on the bottom product I.

The bottom product I, comprising essentially 6-aminocapronitrile, hexamethylenediamine, adiponitrile, hexamethyleneimine, inert compound or compounds A and ammonia, the ammonia content being lower than that of the mixture obtained from the reactor R1, is subjected to a second distillation to give a mixture of the inert compound or compounds A and ammonia as the top product and a bottom product II, the distillation being carried out at a bottom temperature of from 100 to 250° C., preferably from 140 to 200° C., and at from 2 to 15, preferably from 4 to 12, bar, with the proviso that the pressures of the first and of the second column (K2 in the drawing) are matched with one another so that a top temperature of more than 20° C. is obtained at a respective bottom temperature of not more than 250° C. It may also be advantageous to carry out the condensation at the top of the second column at lower temperatures, the top product, which consists of pure or relatively highly concentrated ammonia, being recycled to the first column, or to recycle the top product of the second column in vapor form, after increasing the pressure by means of a compressor, to the first column or to its condenser.

The bottom product II, comprising essentially 6-aminocapronitrile, hexamethylenediamine, adiponitrile, hexamethyleneimine and inert compound or compounds A, is subjected to a distillation in a third column (K3 in the drawing) to give the inert compound or compounds A as the top product and a bottom product III, the distillation being carried out at a bottom temperature of from 50 to 250° C., preferably from 140 to 200° C., and at from 0.05 to 2, preferably from 0.2 to 1, bar, with the proviso that the inert compound or compounds A obtained as the top product is or are fed to the second column, and, if desired, the distillation is carried out in the presence of one or more compounds B which are inert under the distillation conditions and boil at from 20 to 250° C., preferably from 60 to 170° C., at a given pressure of 0.3 bar.

Examples of compounds B are alkanes, cycloalkanes, aromatics, naphthenes, alcohols, ethers, nitrites and amines having the abovementioned properties, in particular di-n-butyl ether, valeronitrile, n-octane, cyclooctane, n-hexylamine, hexamethyleneimine and hexamethylenediamine, preferably hexamethyleneimine and/or hexamethylenediamine, particularly preferably hexamethyleneimine.

In a preferred embodiment, hexamethyleneimine and/or hexamethylenediamine are chosen as compound B or, particularly preferably, no further compound B is added.

Compound B is preferably added to the column K3 in an amount of from 0.01 to 50, preferably from 0.5 to 10, % by weight, based on the bottom product II.

The bottom product III, comprising essentially 6-aminocapronitrile, hexamethylenediamine, adiponitrile, hexamethyleneimine and, if desired, inert compound or compounds B, is subjected to a distillation in a fourth column (K4 in the drawing) to give a top product KP1, containing essentially hexamethyleneimine, if desired inert compound or compounds B and a side stream SA1, comprising essentially hexamethylenediamine, the bottom temperature of the column being from 50 to 250° C. and the pressure from 0.05 to 1.5 bar, and to give a bottom product IV.

If desired, the column is equipped with a dividing wall in the region between feed and side take-off point (Petlyuk column) so that the hexamethylenediamine obtained is essentially free of hexamethyleneimine and inert compound or compounds B and of other low boilers, top product KP1 and/or HMD from the side stream SA1 being fed, if required, to the third column or, if required, only a part thereof being fed to the third column and the remainder being removed.

The bottom product IV, comprising essentially 6-aminocapronitrile and adiponitrile and possibly high boilers, is subjected to a distillation in a fifth column (K5 in the drawing) to give 6-aminocapronitrile having a purity of at least 95%, preferably from 99 to 99.9%, as the top product and a side stream V consisting essentially of adiponitrile and a bottom product V which consists of high boilers and small amounts of adiponitrile.

If desired, the column is equipped with a dividing wall in the region between feed and side take-off point, so that the adiponitrile obtained comprises relatively small amounts of high boilers, the distillation being carried out at a bottom temperature of from 50 to 250° C. and at from 10 to 300 mbar.

Instead of obtaining adiponitrile as side stream V, it is also possible to separate bottom product V from column K5, comprising adiponitrile and higher boiling compounds, by distillation in a further column K6 to obtain adiponitrile as top product VI.

According to the invention, the portion comprising essentially adiponitrile, which in the disclosed distillative workup of the adiponitrile hydrogenation mixture is obtained as side stream V of column K5, as top product VI of column K6 or as bottom product of column K5, preferably as side stream V of column K5 [sic], is treated with an acid or an acidic ion exchanger.

Suitable acids or acidic ion exchangers are primarily substances which can function as proton donors with respect to primary, secondary and tertiary saturated and unsaturated amines such as enamines. Acids having a pKa value of at most 10, preferably at most 7, are particularly suitable.

Suitable acids include inorganic acids such as nitric acid, preferably sulfuric acid, in particular as 100% strength by weight sulfuric acid or as an at least 90% by weight, preferably 96% by weight, mixture especially with water or phosphoric acid, organic acids, for example carboxylic acids such as adipic acid, 2-ethylhexanoic acid, pimelic acid, suberic acid, undecanedioic acid, terephthalic acid, cyclohexanecarboxylic acid, for example sulfonic acid such as p-toluenesulfonic acid, benzenesulfonic acid, acidic ion exchangers such as Lewatit S100G1, Amberlyst 15, Dowex 50 WX 8, Bay. Kat. K 2431, Amberlite IR-120, for example, and also mixtures of such acids and acidic ion exchangers.

The reaction of the adiponitrile with the acid can be effected in the presence of a liquid diluent such as water, in which case the liquid diluent can be added to the adiponitrile together with the acid or before or after the acid.

The direct treatment of adiponitrile which has not been freed from higher boiling compounds, for example the bottom product V of column K5, if it does not contain adiponitrile side stream, is likewise possible. In this case, the consumption of acid or acidic ion exchanger and the amount of residue produced after the adiponitrile has been removed increases.

The molar ratio of acid groups to the basic compounds present in the residue should be at least equimolar, preferably superequimolar. It has been found to be advantageous to add from 0.01 to 10% by weight, in particular from 0.1 to 2% by weight, of acid, based on adiponitrile.

The reaction of the adiponitrile with the acid can be effected in a conventional manner, as by mixing or passing the adiponitrile through a fixed ion exchanger bed, advantageously at temperatures from 2 to 250° C., especially from 30 to 100° C., the resulting reaction times ranging from 1 second to 30 minutes, in particular from 1 second to 10 minutes.

The adiponitrile can be removed from the mixture in a conventional manner, advantageously by distillation or extraction.

If a liquid diluent such as water is added during the reaction of the residue with the acid, the liquid diluent can preferably be removed by adsorption, especially distillation, before the adiponitrile is removed.

Similarly, the reaction products obtained after the acid has been added and any excess acid can advantageously be removed from adiponitrile by extraction, for example with water.

The adiponitrile obtained by the process of this invention can be re-used for partial hydrogenation to hexamethylenediamine and 6-aminocapronitrile without a buildup of by-products which prevent an on-spec production of hexamethylenediamine and/or 6-aminocapronitrile and/or adversely affect the on-stream time of the catalyst for the partial hydrogenation.

The 6-aminocapronitrile can subsequently be processed in a conventional manner, optionally via the intermediate stage of caprolactam, into nylon-6, while hexamethylenediamine can be processed with adipic acid into nylon-6,6. Nylon-6 and nylon-6,6 are industrially important materials of construction.

Abbreviations: ADN=adiponitrile, ACN=6-aminocapronitrile, HMD=hexamethylenediamine

EXAMPLE 1 a) Preparation of Crude ADN

A tubular reactor 2 m in length and 2.5 cm in internal diameter was charged with 750 ml (1534 g) of a catalyst consisting of 90% by weight of CoO, 5% by weight of $Mn_2O_3$, 3% by weight of $P_2O_5$ and 2% by weight of $Na_2O$. The catalyst was subsequently activated over 48 h under atmospheric pressure in a 500 l/h hydrogen stream by raising the temperature from 30° C. to 280° C. At 70° C. the reactor was supplied at 200 bar with a mixture of 400 ml/h adiponitrile, 930 ml/h of ammonia and 500 l/h of hydrogen. After 50 hours the conversion was 67% and the reaction mixture consisted essentially of 32% by weight of ADN, 48% by weight of ACN and 19% by weight of HMD. The hydrogenation effluent was collected for a period of 3000 hours after removal of ammonia.

6-Aminocapronitrile and hexamethylenediamine were removed from the hydrogenation effluent by distillation. Then 2.9 kg/h of adiponitrile were distilled off overhead in a column having 4 theoretical plates at a top-of-column pressure of 20 mbar, leaving 150 g/h of residue behind at the base of the column. The adiponitrile comprised 9400 ppm of bishexamethylenetriamine (BHMTA), 320 ppm of 2-(5-cyanopentylamino)tetrahydroazepine (CPATHA) and 280 ppm of 1-amino-2-cyanocyclopentene (ACCPE).

b) Purification of Crude ADN

After the distillation, the adiponitrile was admixed in a stirred autoclave with 25 g/h of 96% strength $H_2SO_4$ and stirred at room temperature for 10 minutes. Water was then separated from the adiponitrile at 30 mbar as the overhead product of the column, and the adiponitrile was distilled in a subsequent stage at 10 mbar. 100 g/h of residue were left as bottom product. The purified adiponitrile comprised less than 30 ppm of BHMTA, 10 ppm of ACCPE and 30 ppm of CPATHA and was recycled into the partial hydrogenation. Here the conditions of Example 1a) resulted in a reactor effluent comprising 34% of ADN, 49% of ACN and 16% of HMD at a conversion of 64%.

EXAMPLE 2

ADN (2.7 kg/h) removed from the hydrogenation effluent and distilled off overhead according to Example 1a) was admixed in a stirred autoclave with 100 g/h of 25% strength $H_3PO_4$ and stirred at room temperature for 10 minutes. Water was then separated from the adiponitrile at 30 mbar as overhead product of a column having 10 theoretical plates, and the adiponitrile was distilled in a subsequent stage at 10 mbar. 90 g/h of residue were left as bottom product. The purified adiponitrile comprised less than 30 ppm of BHMTA, 30 ppm of CPATHA and 10 ppm of ACCPE and was recycled into the partial hydrogenation. Here no change in the catalyst activity or the ACN/HMD selectivity was found under the conditions of Example 1a).

EXAMPLE 3

ADN removed from the hydrogenation effluent and distilled off overhead according to Example 1a) was passed at room temperature through an acidic ion exchanger (Dowex 50 WX 8). After the ion exchanger, the purified adiponitrile comprised less than 30 ppm of BHMTA, 30 ppm of CPATHA and 10 ppm of ACCPE and was recycled into the partial hydrogenation. Here no change in the catalyst activity or the ACN/HMD selectivity was found under the conditions of Example 1a).

We claim:

1. A process for coproduction of 6-aminocapronitrile and hexa-methylonediamine starting from adiponitrile, which comprises
   (1) partially hydrogenating adiponitrile in the presence of a catalyst to obtain a mixture comprising 6-aminocapronitrile, hexamethylenediamine and adiponitrile,
   (2) removing 6-aminocapronitrile and hexamethylenediamine from the mixture,
   (3) adding to the mixture comprising adiponitrile from 0.01 to 10% by weight of an acid, based on adiponitrile, or an acidic ion exchanger and removing the adiponitrile from the mixture, and
   (4) recycling the adiponitrile into step (1).

2. A process as claimed in claim 1, wherein the adiponitrile is removed from the mixture in step (3) by distillation or extraction.

3. A process as claimed in claim 1, wherein the hydrogenation is carried out in the presence of a liquid diluent.

4. A process as claimed in claim 1 in the presence of a liquid diluent, further comprising removing the liquid diluent between steps (1) and (2).

5. A process as claimed in claim 1, wherein the catalyst used comprises
   (a) a compound based on a metal selected from the group consisting of nickel, cobalt, iron, ruthenium and rhodium,
   (b) from 0.01 to 25% by weight, based on (a), of a promoter based on a metal selected from the group consisting of palladium, platinum, iridium, osmium, copper, silver, gold, chromium, molybdenum, tungsten, manganese, rhenium, zinc, cadmium, lead, aluminum, tin, phosphorus, arsenic, antimony, bismuth and rare earth metals, and
   (c) from 0 to 5% by weight, based on (a), of a compound based on an alkali metal or an alkaline earth metal,
with the proviso that, if a compound based on only ruthenium or rhodium or ruthenium and rhodium or nickel and rhodium is chosen as component (a), said promoter (b) can, if desired, be dispensed with, and with the further proviso that said component (a) shall not be based on iron when said component (b) is aluminum.

6. A process as claimed in claim 1, wherein the catalyst used comprises
   (a) a compound based on iron,
   (b) from 0 to 5% by weight, based on (a), of a promoter based on an element or 2, 3, 4 or 5 elements selected from the group consisting of aluminum, silicon, zirconium, vanadium and titanium, and
   (c) from 0 to 5% by weight, based on (a), of a compound based on an alkali metal or an alkaline earth metal.

7. A process as claimed in claim 1, wherein the adiponitrile is removed from the mixture by distillation and the acid used has a higher boiling point than adiponitrile under the distillation pressure.

8. A process as claimed in claim 1, wherein the acid used has a $pK_a$ value of at most 10.

9. A process as claimed in claim 1, wherein a portion comprising adiponitrile is removed between steps (2) and (3).

10. A process as claimed in claim 1, wherein the acid used in step (3) is sulfuric acid or a mixture comprising at least 90% by weight of sulfuric acid.

11. A process as claimed in claim 5, wherein the catalyst used comprises from 0.1 to 5% by weight, based on (a), of a promoter based on a metal selected from the group consisting of palladium, platinum, iridium, osmium, copper, silver, gold, chromium, molybdenum, tungsten, maganese, rhenium, zinc, cadmium, lead, aluminum, tin, phosphorus, arsenic, antimony, bismuth and rare earth metals.

12. A process as claimed in claim 5, wherein the catalyst used comprises from 0.1 to 3% by weight, based on (a), of a compound based on an alkali metal or an alkaline earth metal.

* * * * *